(12) United States Patent
Schneider et al.

(10) Patent No.: US 8,457,924 B2
(45) Date of Patent: Jun. 4, 2013

(54) CONTROL SYSTEM AND METHOD USING AN ULTRASONIC AREA ARRAY

(75) Inventors: John K. Schneider, Snyder, NY (US); Jack C. Kitchens, Tonawanda, NY (US)

(73) Assignee: Ultra-Scan Corporation, Amherst, NY (US)

( * ) Notice: Subject to any disclaimer, the term of this patent is extended or adjusted under 35 U.S.C. 154(b) by 0 days.

(21) Appl. No.: 13/109,764

(22) Filed: May 17, 2011

(65) Prior Publication Data
US 2011/0282623 A1 Nov. 17, 2011

Related U.S. Application Data

(60) Provisional application No. 61/345,504, filed on May 17, 2010.

(51) Int. Cl.
*G06F 19/00* (2006.01)
(52) U.S. Cl.
USPC ............................. 702/150; 702/39; 702/142
(58) Field of Classification Search
None
See application file for complete search history.

(56) References Cited

U.S. PATENT DOCUMENTS

| | | | |
|---|---|---|---|
| 7,142,699 B2* | 11/2006 | Reisman et al. | 382/124 |
| 2005/0093834 A1 | 5/2005 | Abdallah et al. | |
| 2005/0196022 A1* | 9/2005 | Schneider et al. | 382/124 |
| 2005/0265587 A1* | 12/2005 | Schneider | 382/124 |
| 2006/0241945 A1 | 10/2006 | Morales | |
| 2007/0258628 A1* | 11/2007 | Schneider et al. | 382/124 |
| 2008/0025572 A1* | 1/2008 | Schneider et al. | 382/115 |
| 2008/0092623 A1* | 4/2008 | Lynch et al. | 73/1.82 |
| 2008/0208517 A1* | 8/2008 | Shamaie | 702/142 |
| 2009/0085878 A1 | 4/2009 | Heubel et al. | |

* cited by examiner

*Primary Examiner* — Sujoy Kundu
(74) *Attorney, Agent, or Firm* — Hodgson Russ LLP

(57) ABSTRACT

A computer control system and method is disclosed. Such a system may include a processor and an ultrasonic area-array sensor configured to receive a ridged surface, such as one or more digits of a hand. The processor may be configured to:
(a) acquire a first information set from the sensor, the first information set representing at least a portion of the ridged surface,
(b) acquire a second information set from the sensor, the second information set representing at least a portion of the ridged surface,
(c) compare the first information set with the second information set to identify a common feature of the ridged surface that is present in both the first information set and the second information set,
(d) determine a first position of the common feature using the first information set,
(e) determine a second position of the common feature using the second information set, and
(f) calculate a control measurement by comparing the first position and the second position.

33 Claims, 3 Drawing Sheets

CONTROL SYSTEM AND METHOD USING AN ULTRASONIC AREA ARRAY

CROSS-REFERENCE TO RELATED APPLICATION

This application claims the benefit of priority to U.S. provisional patent application Ser. No. 61/345,504, filed on May 17, 2010.

FIELD OF THE INVENTION

The present invention relates to the use of ultrasound to detect variations of a surface, such as the surface of a finger. The invention also relates to systems for controlling a computer.

BACKGROUND OF THE INVENTION

Many fingerprint readers have a line of sensors which are used to produce a series of information sets about a friction ridge. As long as the finger continues to move across the sensor line, each information set includes a line of information about a different portion of the friction ridge. If the velocity of the finger is known, the series of information sets may be assembled and used to create an image of the fingerprint.

Other fingerprint readers include an array of sensors that are arranged to collect information from an area (as distinguished from a line), which may be defined by a width and a length. Such area-array sensors may have multiple lines of sensors which obtain information about an area of the friction ridge (often at substantially the same time) so that an image of the friction ridge can be created without moving the finger across the sensor array. These biometric scanners have been used to collect information about friction ridge surfaces for the purpose of identifying the user of a computer. Once a user is identified as an authorized user of the computer, the user is then permitted to use the computer, for example by operating a mouse, keyboard, touchpad and other devices in order to interface with and control the computer. However, by requiring a scanner for purposes of biometric authorization, as well as a mouse or touchpad for controlling the computer, the size and cost of a computer system is increased.

SUMMARY OF THE INVENTION

The invention may be embodied as a computer control system. Such a system may include a processor and an ultrasonic area-array sensor configured to analyze a surface, such as a digit of a hand. The surface is ridged, that is to say that the surface is not perfectly flat. The processor may be configured to:

(a) acquire a first information set from the ultrasonic sensor, the first information set representing at least a portion of the ridged surface,
(b) acquire a second information set from the ultrasonic sensor, the second information set representing at least a portion of the ridged surface,
(c) compare the first information set with the second information set to identify a common feature of the ridged surface that is present in both the first information set and the second information set,
(d) determine a first position of the common feature using the first information set,
(e) determine a second position of the common feature using the second information set, and
(f) calculate a control measurement by comparing the first position and the second position.

The control measurement may be used for a number of tasks. For example, the control measurement may be used to control a cursor displayed on a monitor. To illustrate, the cursor may be moved a distance on a computer monitor that is correlated to the distance between the first position and the second position. Also, the pointer may be moved in a direction that is correlated to the direction from the first position to the second position. In this manner, the movement of a finger on a platen of the sensor array may be reflected in the movement of the cursor on the computer monitor.

In addition, the control measurement may be a velocity. The velocity may be the distance between the first position and the second position divided by the time between acquiring the first information set and the second information set. Using the velocity, a cursor on a monitor may be moved at a velocity that correlates to the control measurement.

The control measurement may be a change in rotational orientation of the common feature between the first position and the second position. The change in rotational orientation may be correlated to a change in a computer control variable. For example, the control variable may be an audio volume of a speaker, or a brightness level of a display monitor. To illustrate how such a change might be implemented, when the change in rotational orientation is counterclockwise, the control variable may be decreased, and when the change in rotational orientation is clockwise, the control variable may be increased.

A change in rotational orientation of the common feature may be correlated to a change in a graphical user interface. For example, the change in the graphical user interface may be to navigate forward or backward, depending on the change in rotational orientation. To illustrate, when the change in rotational orientation is clockwise, the graphical user interface may advance one or more pages, and when the change in rotational orientation is counterclockwise, the graphical user interface may go back one or more pages.

The change in rotational orientation may be correlated to selecting an application, or closing an application that is provided by a computer. For example, a clockwise change in the rotational orientation of the common feature may be interpreted as indicating a desire to select an application, while a counterclockwise change in the rotational orientation of the common feature may be interpreted as indicating a desire to close an application provided by the computer.

The change in rotational orientation may cause an interrupt in a software routine being performed. For example, the software routine may be running on a general purpose computer, and the interrupt may cause the routine to be interrupted, so that a different routine can then be executed.

The invention may be implemented as a method of effecting a change in a state of a computer system, and as such the method may be used to make use of the system described above. In one such method, the area-array ultrasonic sensor and the processor are provided, the first and second information sets are acquired from the ultrasonic sensor, and the information sets are compared to identify a common feature of the ridged surface that is present in both the first information set and the second information set. A first position of the common feature and a second position of the common feature are determined using the first and second information sets, respectively. A control measurement is calculated by comparing the first position and the second position, and the control measurement may be used to effect a change in a state of a computer system. For example, the change in state may be to change the position of an object, such as a cursor, that is displayed on a monitor of the computer system.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF THE INVENTION

Figure 1:
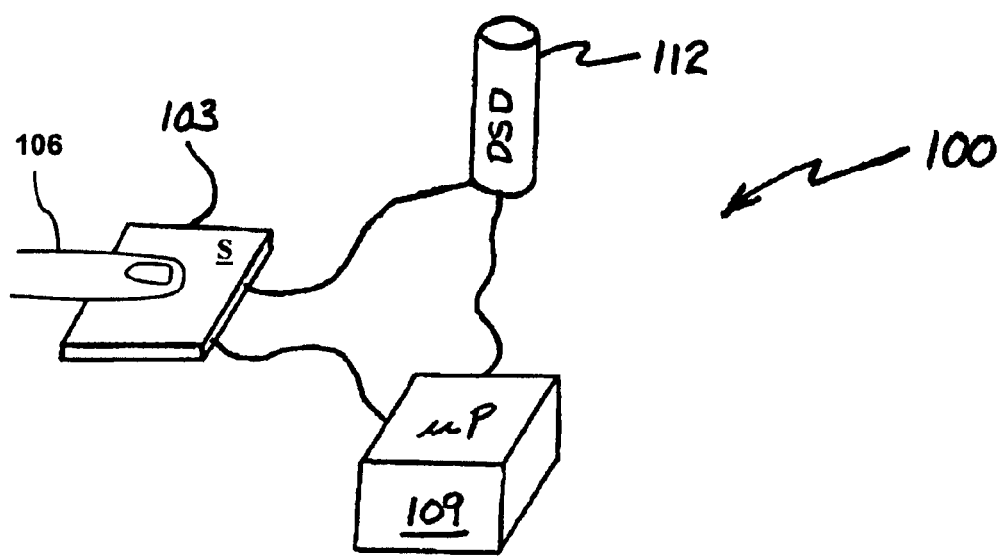
FIG. 1 is a schematic of a system according to the invention.

FIG. 1 depicts a control system 100 according to the invention. To make optimum use of the physical space available on some small consumer appliances, especially those that require a fingerprint scanner, it may be useful to provide an ultrasonic area-array biometric sensor 103, such as a fingerprint scanner, and use the information produced by the sensor 103 not only for authorizing use of the computer, but also to control the computer. It should be noted that the invention is described sometimes with regard to the friction ridge of a human digit, but the invention may be implemented using other ridged surfaces. For example, a person's finger nail or a stylus may provide the ridged surface.

In one embodiment of the invention, the ultrasonic area-array biometric sensor 103 captures information about a ridged surface, such as a friction ridge of a finger 106, and then provides information about the ridged surface. For example, the friction ridge information may be used to provide mouse-type functionality such as the ability to identify and select icons displayed on a monitor. In this manner, biometric information gathered by the sensor 103 can be used to control a cursor, which may take the form of a pointer, displayed on a monitor, and control the computer.

Figure 2:
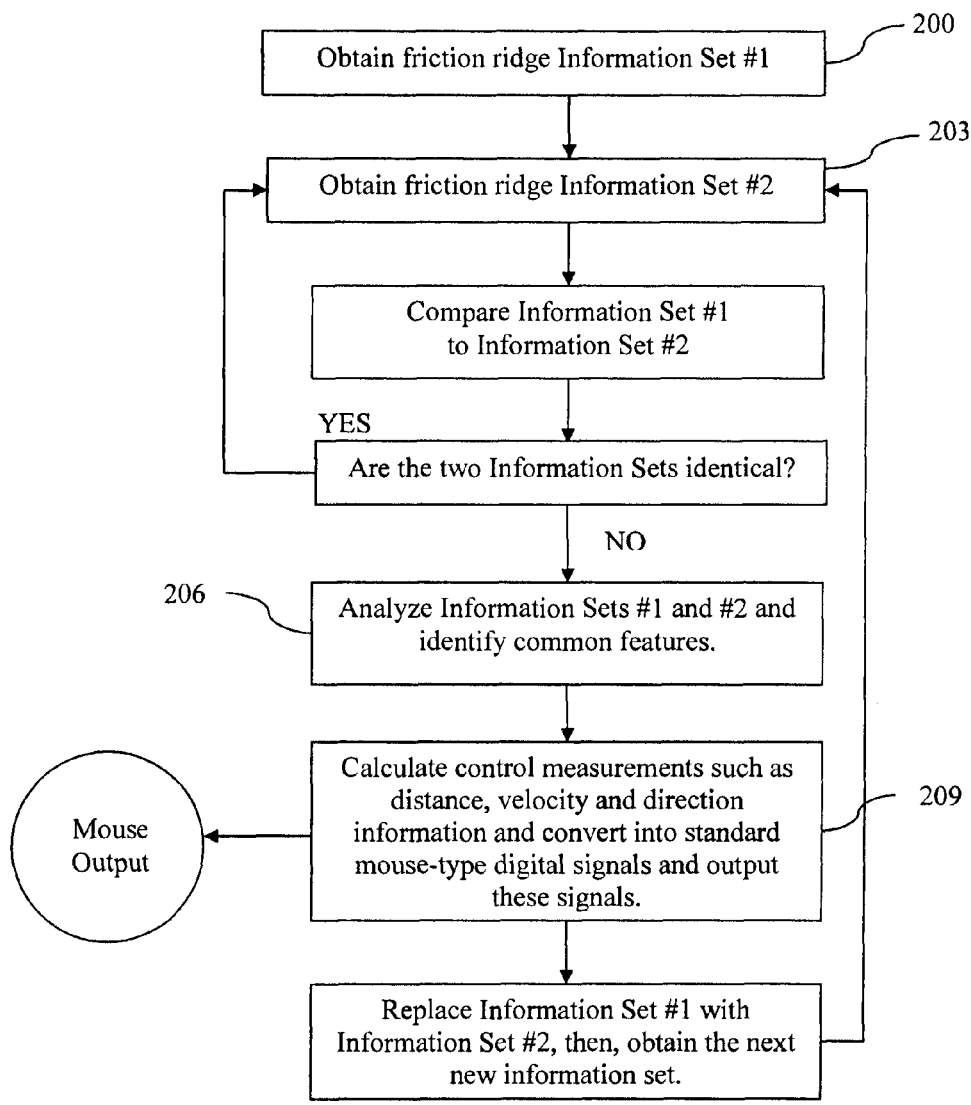
FIG. 2 is flow chart depicting a method that is in keeping with the invention.

FIG. 1 is a schematic of a system that is in keeping with the invention. A flowchart of a method according to the invention appears in FIG. 2. In a system 100 according to the invention, the ultrasonic area-array sensor 103, under the control of a processor 109, may be used to collect 200, 203 a series of information sets, each of which describe the position of a ridged surface, such as a friction ridge. The information sets may be stored on a data storage device 112. Although the information sets may be used to create a sequence of images of the ridged surface, creation of the image is not necessarily required. As the finger is moved, the sensor periodically obtains information sets, and these sets may be analyzed 206 to identify features of the ridged surface that are common to the sets, and then one or more control measurements, such as distance, velocity or direction information, may be calculated 209. The control measurements may be used in lieu of a mouse to effect a change in the state of a graphical user interface that is displayed on a monitor.

In operation, a system according to the invention may capture information about a ridged surface while the ridged surface is moving across a platen that covers an ultrasonic area-array of sensors. The captured information can be used to create a first information set corresponding to (for example) a friction ridge at a first time, and the captured information can be used to create a second information set corresponding to the friction ridge at a second time. One or more features that are common to each information set may be identified. The position of a common feature in the first information set may be compared to the position of that common feature in the second information set, and these two positions may be used to determine information about the movement of the friction ridge surface, such as the direction in which the friction ridge (and hence the finger) was moving. The direction in which the finger was moving may be thought of as a vector having its tail at the location of the common feature in the first information set, and its head at the location of the common feature in the second information set.

Information about the movement of the friction ridge surface may include the velocity of the finger, which may be determined by (i) calculating the distance between the location of the common feature in the first information set and the location of the common feature in the second information set, (ii) calculating the time difference between obtaining the first information set and the second information set, and (iii) dividing the distance by the time difference.

The direction and velocity information may be interpreted as indicating a person's desire to move a cursor displayed on a monitor in a certain manner. In this manner, the ultrasonic area-array sensor may be used in lieu of a mouse to move a cursor on a graphical user interface, and ultimately to select icons that are displayed via the graphical user interface. The ultrasonic area-array sensor and monitor may be associated with a computer that is part of a cell phone or personal digital assistant in order to move a cursor that is used for identifying objects displayed on the monitor.

It is possible to determine not only the location of a common feature, but also the orientation of a common feature. In addition, by identifying more than one common feature, the relative orientation of the features with respect to the ultrasonic area-array sensor may be determined. The orientation of one common feature, and the relative orientation of more than one common features, is referred to collectively as the common feature orientation, even though there may be more than one common feature involved. By knowing the common feature orientation, it is possible to determine how the ridged surface was rotated between the time the first information set was obtained and the time the second information set was obtained.

To illustrate the concept, consider that if two information sets are each used to create an image of a friction ridge surface, a line extending between two features in the image of the first information set may not have the same angular orientation as a line drawn between the same two features in the image of the second information set. The rotational shift between the two lines may be considered as an indicator as to how the friction ridge rotated between the two times.

Rotation of the ridged surface may be used to indicate various desires of the user. For example, a clockwise rotation of the friction ridge may indicate that the user desires to select an icon, and a counter-clockwise rotation of the friction ridge may indicate a desire to return to a prior "level" or display of the graphical user interface that is provided via the monitor. As such, if the user desires to use the telephone feature of her personal digital assistant, then by starting at the main menu of the graphical user interface, the user may move her finger over the ultrasonic area-array until a pointer on the monitor is coincident with a telephone icon that is displayed as part of the main menu. Then, by rotating her finger more than a threshold amount (e.g. 15 degrees), the telephone icon may be selected. In response to selecting the telephone icon, the user may be provided with a display that prompts the user to enter a phone number. If the user then changes her mind and decides that the telephone feature is not desired, she may rotate her finger counter-clockwise, and the system will interpret that rotation as a desire to return to the main menu.

Figure 3:
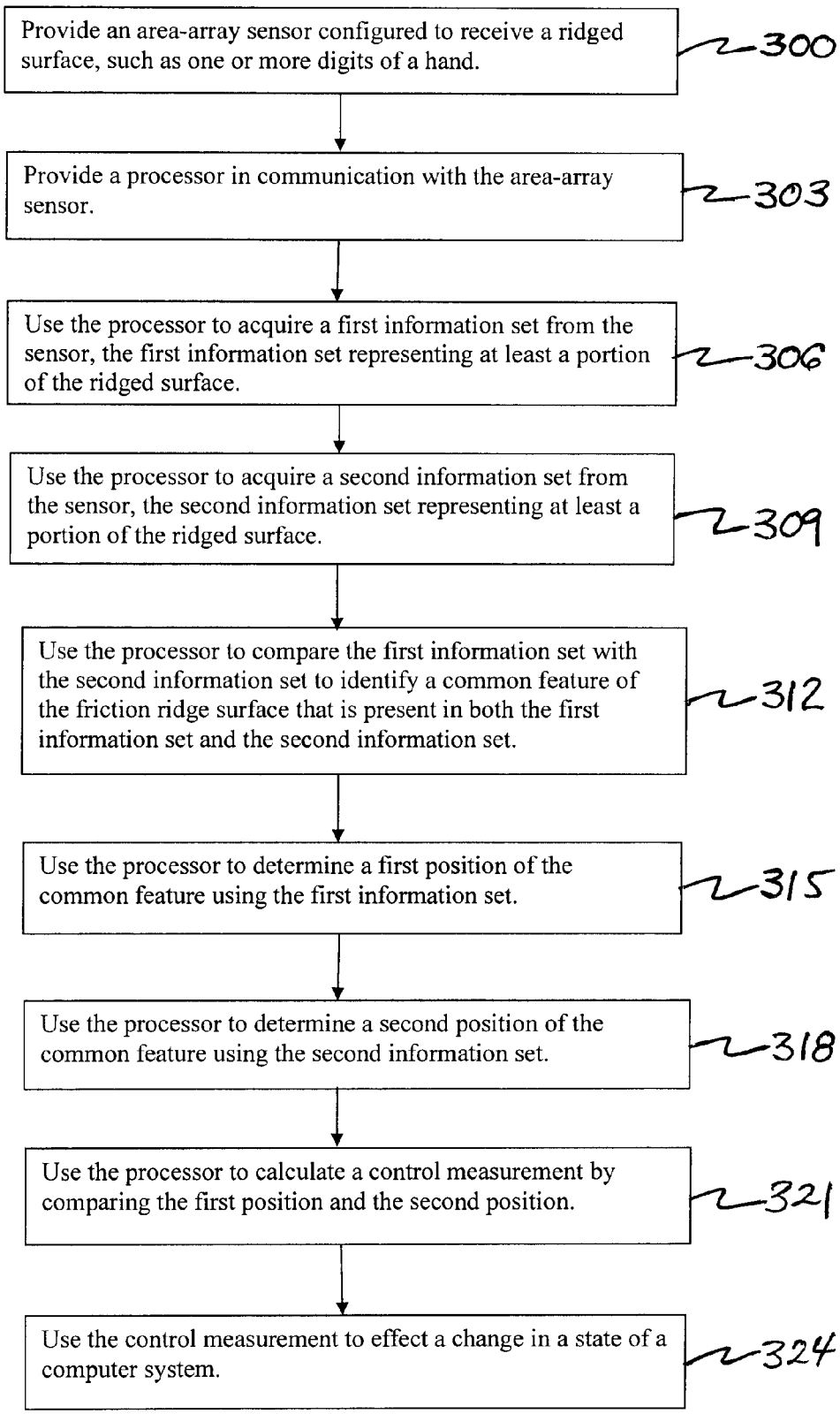
FIG. 3 is flow chart depicting a method that is in keeping with the invention.

Having described embodiments of the invention above, we now proceed to provide additional detail about a particular method that is in keeping with the invention, and in doing so, we also describe a system that is in keeping with the invention. FIG. 3 is a flowchart depicting steps that are in keeping with the method. The method may be implemented to effect a change in a state of a computer system. In that method, an ultrasonic area-array sensor may be provided 300, and a processor may be provided 303. The sensor may be configured to receive a ridged surface, such as one or more digits of a hand. The processor may be configured, for example via software, to:

(a) acquire 306 a first information set from the sensor, the first information set representing at least a portion of the ridged surface,
(b) acquire 309 a second information set from the sensor, the second information set representing at least a portion of the ridged surface,
(c) compare 312 the first information set with the second information set to identify a common feature of the ridged surface that is present in both the first information set and the second information set,
(d) determine 315 a first position of the common feature using the first information set,
(e) determine 318 a second position of the common feature using the second information set, and
(f) calculate 321 a control measurement by comparing the first position and the second position.

The control measurement may be used 324 to effect a change in a state of a computer system. In the paragraphs that follow, we describe some of the changes in state that may be effected.

Position change: The change in state may be a change to a cursor displayed on a monitor of the computer system. For example, the change in state may be a change in the position of an object displayed on a monitor of the computer system, and the control measurement may be a distance between the first position and the second position. The distance between the first position and the second position may be correlated to the position change.

Direction change: The change in state may be a change to a cursor displayed on a monitor of the computer system. For example, the change in state may be a change in the direction in which the cursor displayed on a monitor is moving, and the control measurement may be a change in direction between the first position and the second position. In this situation, the control measurement is a direction from the first position to the second position. The direction from the first position to the second position may be correlated to the direction change.

Velocity: The change in state may be a change to a cursor displayed on a monitor of the computer system. For example, the change in state may be a change in the velocity of a cursor displayed on a monitor of the computer system, and the control measurement may be a velocity of a friction ridge between the first position and the second position. In this situation, the control measurement is a velocity of the friction ridge, the velocity being the distance between the first position and the second position divided by the time between acquiring the first information set and the second information set. The friction ridge velocity may be correlated to the velocity of the object that is displayed on the monitor.

Control Variable: The control measurement may be a change in rotational orientation of the common feature of the ridged surface between the first position and the second position. In such a situation, the change in state may be a change in a computer control variable. For example, the control variable may be a volume level of an audio speaker, or a brightness level of a display monitor. It may be possible to configure the processor so that when the change in rotational orientation is counterclockwise, the control variable is decreased. Also, it may be possible to configure the processor so that when the change in rotational orientation is clockwise, the control variable is increased.

GUI: The change in state may be a change in a graphical user interface. In such a situation, the change in the graphical user interface may be to navigate forward when the change in rotational orientation of the ridged surface is clockwise. Also, the change in the graphical user interface may be to navigate backward when the change in rotational orientation of the ridged surface is counterclockwise.

Selection/Closing: The change in state may be selection of an application provided by a computer. Also, the change in state may be closing an application provided by a computer. For example, when the control measurement is a clockwise rotation of the ridged surface, the application identified by the location of the cursor may be opened. When the control measurement is a counterclockwise rotation of the ridged surface, the application that is currently opened or identified by the cursor may be closed.

Interrupt Routine: The change in state may be to interrupt a routine being executed by the computer. For example, when the control measurement is a clockwise rotation of the ridged surface, the routine currently being run on the computer may be interrupted so that a different routine may be started. In this manner, the operation of the computer may be controlled.

By using a single area-array sensor to provide information sets that can be used both for biometric identification and for conveying control instructions to a computer, the size and cost of implementing these capabilities into an electronic device can be reduced. In this manner, devices such as cell phones, laptop computers and personal digital assistants may be provided with the ability to authorize use of such a device using biometric identification, and to control the device according to the user's desires.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A computer control system, comprising:
an ultrasonic area-array sensor configured to receive a ridged surface;
a processor configured to:
(a) acquire a first information set from the sensor, the first information set representing at least a portion of the ridged surface,
(b) acquire a second information set from the sensor, the second information set representing at least a portion of the ridged surface,
(c) compare the first information set with the second information set to identify a common feature of the ridged surface that is present in both the first information set and the second information set,
(d) determine a first position of the common feature using the first information set,
(e) determine a second position of the common feature using the second information set, and
(f) calculate a control measurement by comparing the first position and the second position, wherein the control measurement is a change in rotational orientation of the common feature between the first position and the second position.

2. The system of claim 1, wherein the control measurement is used to control a cursor displayed on a monitor.

3. The system of claim 1, wherein the control measurement is a distance between the first position and the second position.

4. The system of claim 1, wherein the control measurement is a direction from the first position to the second position.

5. The system of claim 1, wherein the control measurement is a velocity, the velocity being the distance between the first position and the second position divided by the time between acquiring the first information set and the second information set.

6. The system of claim 1, wherein the change in rotational orientation is correlated to a change in a computer control variable.

7. The system of claim 6, wherein the control variable is an audio volume level.

8. The system of claim 6, wherein the control variable is a brightness level.

9. The system of claim 6, wherein when the change in rotational orientation is counterclockwise, the control variable is decreased.

10. The system of claim 6, wherein when the change in rotational orientation is clockwise, the control variable is increased.

11. The system of claim 1, wherein the change in rotational orientation is correlated to a change in a graphical user interface.

12. The system of claim 11, wherein the change in the graphical user interface is to navigate forward when the change in rotational orientation is clockwise.

13. The system of claim 11, wherein the change in the graphical user interface is to navigate backward when the change in rotational orientation is counterclockwise.

14. The system of claim 1, wherein the change in rotational orientation is correlated to selecting an application provided by a computer.

15. The system of claim 14, wherein the change in rotational orientation is correlated to closing an application provided by a computer.

16. The system of claim 14, wherein the change in rotational orientation causes an interrupt for a remote device.

17. The system of claim 16, wherein the remote device is a general purpose computer.

18. A method of effecting a change in a state of a computer system, comprising:
providing an ultrasonic area-array sensor configured to receive a ridged surface;
providing a processor configured to:
(a) acquire a first information set from the sensor, the first information set representing at least a portion of the ridged surface,
(b) acquire a second information set from the sensor, the second information set representing at least a portion of the ridged surface,
(c) compare the first information set with the second information set to identify a common feature of the ridged surface that is present in both the first information set and the second information set,
(d) determine a first position of the common feature using the first information set,
(e) determine a second position of the common feature using the second information set, and
(f) calculate a control measurement by comparing the first position and the second position, wherein the control measurement is a change in rotational orientation of the common feature between the first position and the second position; and
using the control measurement to effect a change in a state of a computer system.

19. The method of claim 18, wherein the change in state is a change to a cursor displayed on a monitor of the computer system.

20. The method of claim 18, wherein the change in state is a position change to an object displayed on a monitor of the computer system, and the control measurement is a distance between the first position and the second position, and the distance is correlated to the position change.

21. The method of claim 18, wherein the change in state is a direction change to an object displayed on a monitor of the computer system, and the control measurement is a direction from the first position to the second position, and the direction is correlated to the direction change.

22. The method of claim 18, wherein the change in state is a velocity of an object displayed on a monitor of the computer system, and the control measurement is a velocity of the ridged surface, the ridged surface velocity being the distance between the first position and the second position divided by the time between acquiring the first information set and the second information set, and the ridged surface velocity is correlated to the displayed object velocity.

23. The system of claim 18, wherein the change in rotational orientation is correlated to a change in a computer control variable.

24. The method of claim 23, wherein the control variable is an audio volume level.

25. The method of claim 23, wherein the control variable is a brightness level.

26. The method of claim 23, wherein when the change in rotational orientation is counterclockwise, the control variable is decreased.

27. The method of claim 23, wherein when the change in rotational orientation is clockwise, the control variable is increased.

28. The system of claim 18, wherein the change in rotational orientation is correlated to a change in a graphical user interface.

29. The method of claim 28, wherein the change in the graphical user interface is to navigate forward when the change in rotational orientation is clockwise.

30. The method of claim 28, wherein the change in the graphical user interface is to navigate backward when the change in rotational orientation is counterclockwise.

31. The system of claim 18, wherein the change in rotational orientation is correlated to selecting an application provided by a computer.

32. The method of claim 18, wherein the change in state is closing an application provided by a computer.

33. The method of claim 18, wherein the change in state is to interrupt a routine being executed by the computer.

* * * * *

UNITED STATES PATENT AND TRADEMARK OFFICE
CERTIFICATE OF CORRECTION

PATENT NO. : 8,457,924 B2
APPLICATION NO. : 13/109764
DATED : June 4, 2013
INVENTOR(S) : Schneider et al.

It is certified that error appears in the above-identified patent and that said Letters Patent is hereby corrected as shown below:

Title page, item (73), the Assignee should read:

--QUALCOMM Incorporated, San Diego, CA (US)--.

Signed and Sealed this
Twenty-fourth Day of September, 2013

Teresa Stanek Rea
*Deputy Director of the United States Patent and Trademark Office*